United States Patent [19]

Mehra

[11] Patent Number: 5,170,802
[45] Date of Patent: Dec. 15, 1992

[54] IMPLANTABLE ELECTRODE FOR LOCATION WITHIN A BLOOD VESSEL

[75] Inventor: Rahul Mehra, Stillwater, Minn.

[73] Assignee: Medtronic, Inc., Minneapolis, Minn.

[21] Appl. No.: 638,247

[22] Filed: Jan. 7, 1991

[51] Int. Cl.⁵ .................................. A61N 1/05
[52] U.S. Cl. ............................ 128/784; 128/785
[58] Field of Search .......................... 128/784–786, 128/788, 419 D, 419 P

[56] References Cited

U.S. PATENT DOCUMENTS

| | | |
|---|---|---|
| Re. 27,652 | 5/1973 | Mirowski . |
| 3,942,536 | 3/1976 | Mirowski et al. . |
| 4,161,952 | 7/1979 | Kinney et al. . |
| 4,481,953 | 11/1984 | Gold et al. . |
| 4,641,656 | 2/1987 | Smits . |
| 4,708,145 | 11/1987 | Tacken, Jr. et al. . |
| 4,727,877 | 3/1988 | Kallok . |
| 4,830,003 | 5/1989 | Wolff et al. . |
| 4,886,062 | 12/1989 | Wiktor . |
| 4,932,407 | 6/1990 | Williams . |
| 5,010,895 | 4/1991 | Maurer et al. ............ 128/788 |
| 5,016,808 | 5/1991 | Heil, Jr. et al. ......... 128/785 X |

FOREIGN PATENT DOCUMENTS 2579469 10/1986 France ..................... 128/786

*Primary Examiner*—Lee S. Cohen
*Attorney, Agent, or Firm*—Reed A. Duthler; Harold R. Patton

[57] ABSTRACT

An expandable electrode for location within a blood vessel or other tubular organ. The electrode takes the form of a hollow, tubular metal structure, expanded into contact with the inner walls of the tubular structure in which the electrode is to be located. Expansion of the electrode may take place by means of plastic deformation of the electrode, or the electrode may be fabricated such that it resiliently expands. The electrode is particularly adapted for location within arteries and veins, and in particular for use in the coronary sinus and great vein of the human heart.

9 Claims, 3 Drawing Sheets

IMPLANTABLE ELECTRODE FOR LOCATION WITHIN A BLOOD VESSEL

BACKGROUND OF THE INVENTION

This invention relates to implantable electrodes generally and to implantable defibrillation electrodes more particularly.

Over the past 20 years there has been substantial work toward development of a practical, implantable defibrillator. Early conceptions of implantable defibrillators, such as disclosed in Reissue Pat. No. 27,652 by Mirowski et al, envision a system employing a ventricular endocardial electrode and a plate electrode mounted directly to the heart, subcutaneously, or to the skin. However, it was recognized early on that a totally transvenous system would be desirable in order to simplify the use of implantable defibrillators. One such system is suggested in U.S. Pat. No. 3,942,536 by Mirowski et al, which discloses a transvenous lead having electrodes intended for location in the right ventricular apex and superior vena cava. Such systems were eventually tested in human beings, with some success. However, currently available commercial versions of implantable defibrillators typically employ epicardial patch electrodes alone or in conjunction with transvenous electrodes.

While systems employing transvenous endocardial electrodes in combination with epicardial patch electrodes are workable, a thoracotomy is still required in order to apply the epicardial electrode. It is generally believed that it would be highly desirable to produce an implantable defibrillator system which would entirely avoid the necessity of a thoracotomy, and there has been substantial work directed towards such systems, as disclosed in U.S. Pat. No. 4,727,877 issued to Kallok and in U.S. Pat. No. 4,708,145 issued to Tacker et al. Both the Tacker et al and Kallok patents disclose the use of a transvenous, two electrode lead in combination with a subcutaneous patch electrode.

Transvenous ventricular defibrillation electrodes are shown in the above cited Mirowski patents and in the Tacker and Kallok patents cited above. Other endocardial defibrillation electrodes are disclosed in U.S. Pat. No. 4,481,953 issued to Gold et al, U.S. Pat. No. 4,161,952 issued to Kinney et al and U.S. Pat. No. 4,641,656 issued to Smits. The Kinney, Smits, and Kallok patents also disclose transvenous defibrillation electrodes intended for use in or adjacent to the coronary sinus.

Electrode systems comprising only transvenously applied electrodes, or electrodes applied transvenously in conjunction with subcutaneous electrodes are also disclosed in U.S. Pat. No. 4,932,407 issued to Williams on Jun. 12, 1990. This patent is incorporated herein by reference in its entirety and discloses elongated coronary sinus electrodes intended for insertion in the coronary sinus and great vein, for use in conjunction with right ventricular defibrillation electrodes, superior vena cava defibrillation electrodes and/or subcutaneous patch electrodes.

SUMMARY OF THE INVENTION

The coronary sinus electrode leads illustrated in Smits and Williams, like prior leads for location in the coronary sinus, have taken the general form of an elongated insulated lead body which carries one or more electrodes located on or exposed to the exterior of the lead body. When such electrode leads are inserted into blood vessels, there is a diminution in the cross sectional area available for blood flow. It is felt that an electrode design which allows for normal blood flow through the blood vessel in which it is implanted would be desirable, particularly in the context of long-term implant of defibrillation electrode leads in the coronary, venous and arterial systems.

The present invention provides an electrode which takes the form of an expandable, hollow, cylindrical conductive body inserted into the vessel in which the electrode is to be located and which is expanded into contact with the interior surface of the blood vessel, in a fashion similar to a class of devices known as endovascular stents. The electrode may take the form of a bent wire electrode located around the expandable portion of a delivery catheter, and expanded by the catheter into contact with the interior of the blood vessel, much is disclosed in U.S. Pat. No. 4,886,062 issued to Wiktor on Dec. 12, 1989, incorporated herein by reference in its entirety. Alternatively, the electrode may take the form of a generally tubular, resilient conductive member compressed into a catheter for introduction. On removal from the catheter, the electrode may expand against the sides of the blood vessel, much as illustrated in U.S. Pat. No. 4,830,003 issued to Wolff et al on May 6, 1989, also incorporated herein by reference in its entirety.

Generally is required that the electrode be expandable from a first configuration in which the outer diameter of the electrode is less than the inner diameter of the vessel to a second configuration having an increased outer diameter and having an inner lumen extending therethrough, which has an inner diameter approximately equal to the inner diameter of the vessel.

Regardless of what form the electrode takes, it is coupled to an elongated insulated conductor, extending from the electrode, and provided with an electrical connector to couple the electrode to an implantable electrical stimulator. In general, it is preferable that the elongated conductor be as small in diameter as is feasible. The lead may comprise only a single expandable or resilient element or may include a plurality of resilient or expandable elements, coupled to individual conductors or coupled to a common conductor. Similarly, more than one electrode lead can be used in the same blood vessel, with electrodes located adjacent to or spaced from one another, depending on the particular application.

Electrodes of this general type are believed to be applicable to all types of stimulation wherein location of the electrode in a tubular structure within the body is desirable. Such other applications may, for example, include muscle stimulation, nerve stimulation, cardiac pacing, cardioversion and defibrillation. In all applications, the electrode has the advantage that flow through the tubular structure (e.g. blood flow through a vein or artery) is still possible with the electrode in place. Further, problems associated with dislodgement of the electrodes should be minimal or non-existent, due to the engagement of the electrode with the surrounding tissue.

DETAILED DESCRIPTION OF THE PREFERRED EMBODIMENT

Figure 1:
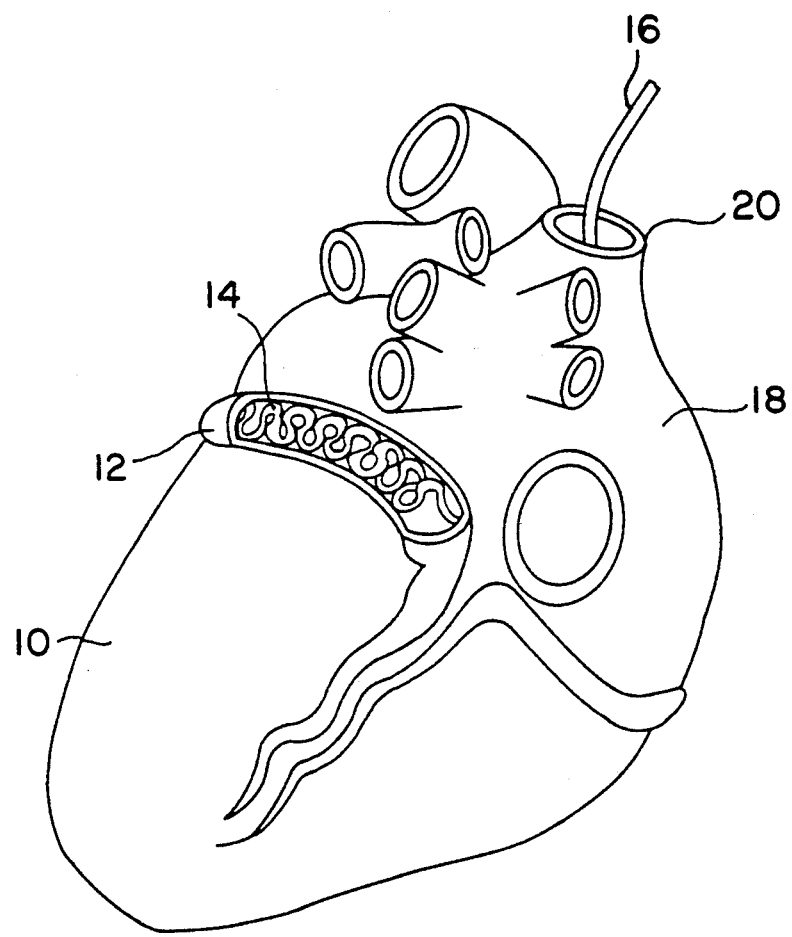
FIG. 1 is a cutaway view of a human heart, illustrating the location of an electrode lead according to the present invention wherein the electrode is located in the coronary sinus.

FIG. 1 shows a posterior view of the heart with the external wall of the coronary sinus 12 cut away to show the electrode portion 14 of a lead according to the present invention, as installed. The electrode 14 is coupled to an elongated insulated conductor 16 which passes through the right atrium 18 and exits the heart through the superior vena cava 20.

Electrode 14 as illustrated takes the form of an expandable cylindrical electrode corresponding in external configuration generally to the intravascular stent illustrated in U.S. Pat. No. 4886062 issued to Wiktor, Inc. herein by reference in its entirety. Alternatively, electrode 14 may take the form of any generally cylindrical expandable or resilient metal member configured such that when expanded, a central lumen through the cylindrical structure is defined to allow for blood flow. Alternate embodiments of an appropriate electrode for use in conjunction with the lead according to the present invention are illustrated in FIGS. 2-4 and 5-6.

Figure 2:
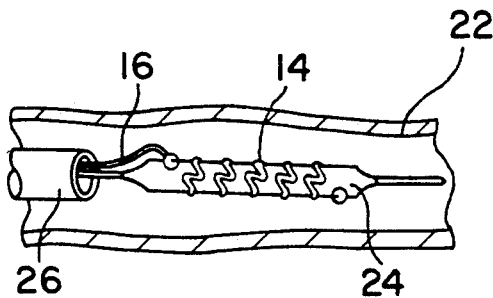
FIG. 2 shows the insertion of an electrode lead according to the present invention having an expandable electrode into a blood vessel.
Figure 3:
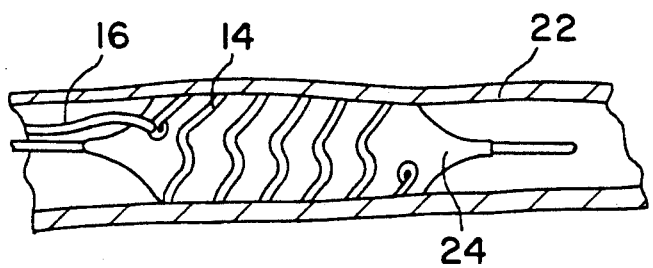
FIG. 3 shows the expansion of the electrode into contact with the wall of the blood vessel.
Figure 4:
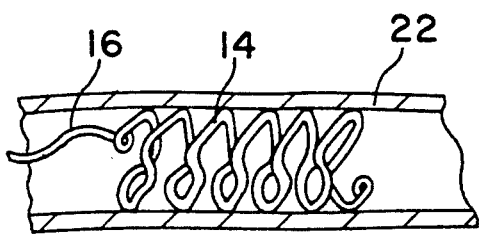
FIG. 4 shows the electrode lead, as implanted in the blood vessel.

FIGS. 2-4 illustrate the installation of a lead according to the present invention employing an expandable hollow cylindrical metal member. The configuration of the electrode 14 is such that the wire of which it is formed is initially preformed into a two-dimensional zigzag form, and subsequently wrapped around a suitable mandrel to provide a hollow cylindrical structure having an external diameter less than the internal diameter of the blood vessel 22 in which it is intended to be implanted. The electrode 14 is coupled to an elongated insulated conductor 16. Electrode 14 is mounted around the expandable portion 24 of a balloon catheter, delivered by means of a guide catheter 26. Upon the guide catheter 26 reaching a position adjacent the desired location of the electrode 14, the balloon catheter is advanced out of the distal end of the guide catheter until the expandable balloon portion 24 of the balloon catheter is located at the desired location of electrode 14.

As illustrated in FIG. 3, following proper location of electrode 14, the expandable balloon portion 24 of the balloon catheter is expanded to urge the electrode 14 into contact with the inner wall of blood vessel 22. Expansion of the electrode 14 causes some permanent deformation of the electrode by straightening of the zigzag bends, which allows the electrode 14 to remain in contact with the interior of blood vessel 22 after deflation of the expandable portion 24 of the balloon catheter. After deflation of the balloon catheter 25, it is withdrawn, leaving the electrode 14 in place, as illustrated in FIG. 4. The electrode 14 now provides an elongated conductive surface taking the general form of a hollow cylinder, having an internal lumen corresponding in internal diameter generally to the internal diameter of the blood vessel 22 in which it is implanted. This allows for the implantation of a large surface area electrode, of the type generally appropriate for defibrillation, cardioversion or other stimulation, without substantially impeding the flow of blood through the blood vessel.

Figure 5:
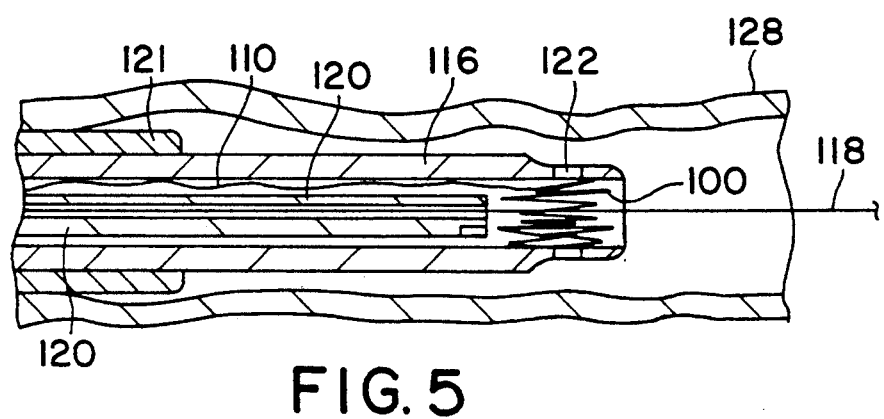
FIG. 5 shows insertion of a lead employing a resilient electrode according to the present invention into a blood vessel.
Figure 6:
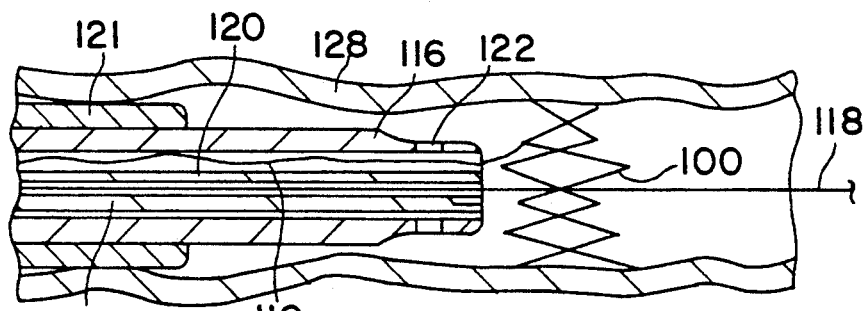
FIG. 6 shows expansion of the resilient electrode into contact with the wall of the blood vessel.

FIGS. 5 and 6 illustrate the installation of a lead employing a resilient electrode. This electrode takes the general physical configuration of the intravascular stent illustrated in U.S. Pat. No. 4,830,003 issued to Wolff et al, also incorporated herein by reference in its entirety. In this embodiment of the invention, the electrode 100 takes the form of a hollow tubular structure formed either by bending metal wires into a zigzag form or by welding short segments of wire into a tubular, zigzag formation as illustrated in the Wolff et al patent. In this case, the stent is formed so that in its relaxed state it displays an outer diameter somewhat in excess of the inner diameter of the blood vessel in which it is to be implanted. Thus, when allowed to expand, it will urge itself against the inner wall of the blood vessel, anchoring the electrode in place.

FIG. 5 shows the electrode 100, coupled to an elongated insulated conductor 110, mounted within a delivery system, and located within a blood vessel 128. The delivery system comprises an outer catheter 116 and an inner catheter 120, mounted within a guide catheter 121. The inner and outer catheters are passed through the guide catheter until the distal end of the outer catheter 116 is located in the location desired for installation of the electrode 100. At this point, the outer catheter 116 is pulled proximately, with the inner catheter 120 holding the electrode 100 in place. When outer catheter 116 is pulled back even with inner catheter 120, electrode 100 expands into contact with the inner surface of blood vessel 128, defining a hollow cylindrical electrode with a cylindrical passage there through which corresponds generally in diameter to the inner diameter of the blood vessel 128. This provides an electrode which does not substantially impede flow of blood through the blood vessel 128. After location of the electrode 100, the delivery system is withdrawn, and the insulated conductor 110 is coupled to an implantable pulse generator such as an implantable defibrillator, cardioverter, pacemaker or other stimulator.

The electrodes illustrated in the two embodiments shown should be fabricated of conductive, biocompatible metals having a low resistivity. For resilient or expandable electrodes of the sort illustrated in FIGS. 2-6, either tantalum or, a stainless steel type alloy such as PM 35N will be appropriate. While both embodiments illustrate the use of a single cylindrical electrode in conjunction with a lead according to the present invention, it is within the scope of the invention to either provide a single insulated conductor coupled to a plurality of expandable cylindrical electrodes, or to install a plurality of expandable electrodes, each with its own insulated conductor, so that the individual electrodes located within the blood vessel may be activated sequentially or such that a stimulation pulse may be delivered between two electrodes located within the same vessel.

Further, while specific embodiments are provided with regard to an expandable and a resilient electrode, other similar structures are believed to be appropriate for use in conjunction with a lead according to the present invention. For example, expandable electrodes taking the form of expandable tubular metal meshes, expandable spirals and so forth are also believed workable in conjunction with the present invention. As such, the embodiments illustrated should be considered exemplary, rather than limiting with respect to the following claims.

In conjunction with the above specification, I claim:

1. A method of inserting an electrode into a desired tubular organ within the body, said tubular organ having an inner surface defining an inner diameter, comprising:

selecting an electrode taking the form of a hollow, elongated conductive cylinder defining a central lumen therethrough, said electrode displaying an outer diameter less than the innter diameter of said tubular organ;

inserting said electrode into said tubular organ at a desired location; and expanding said electrode into contact with the inner surface of said tubular organ by permanently deforming said electrode by expanding said electrode from a first configuration in which the other diameter of said electrode is substantially less than the inner diameter of said tubular organ to a second configuration in which the lumen through said electrode has an inner diameter approximately equal to the inner diameter of said tubular organ.

2. A method according to claim 1 wherein said step of inserting said electrode comprises mounting said electrode to a catheter having an expansible portion, such that the expansible portion of said catheter is located within said lumen through said electrode; and wherein said step of expanding said electrode comprises expanding said expansible portion of said catheter to accomplish said permanent deformation of said electrode.

3. A method according to claim 1 wherein said step of inserting said electrode into said desired tubular organ comprises inserting said electrode into a blood vessel within said body.

4. A method according to claim 3 wherein said step of inserting said electrode into said desired tubular organ comprises inserting said electrode into the coronary sinus within said body.

5. An implantable electrical lead, comprising:

an elongated insulated conductor having a proximal end and distal end;

a hollow, cylindrical electrode formed of a permanently deformable material, mounted to the distal end of said conductor and extending distally therefrom, said cylindrical electrode having a central lumen extending therethrough, said cylindrical electrode expandable from a first configuration displaying a first outer diameter to a second configuration displaying an increased, second outer diameter wherein said electrode is adapted to be permanently deformed by expansion from said first diameter to said second diameter.

6. An electrical lead according to claim 5 further comprising a delivery catheter having an expandable portion located thereon, wherein said electrode is mounted to said delivery catheter such that said cylindrical electrode is mounted around said expandable portion of said catheter.

7. An electrical lead according to claim 5 wherein said hollow, cylindrical electrode comprises an electrode formed entirely of a conductive material.

8. An implantable electrical lead according to claim 7 wherein said electrode is fabricated entirely of a conductive metal.

9. An electrical lead according to claim 5 wherein said electrode is fabricated of conductive metal wire.

* * * * *